(12) United States Patent
Abboud

(10) Patent No.: US 10,463,580 B2
(45) Date of Patent: Nov. 5, 2019

(54) DENTAL TREATMENT METHOD AND ABUTMENT USED THEREIN

(71) Applicant: THE RESEARCH FOUNDATION FOR THE STATE UNIVERSITY OF NEW YORK, Albany, NY (US)

(72) Inventor: Marcus Abboud, Stony Brook, NY (US)

(73) Assignee: The Research Foundation for The State University of New York, Albany, NY (US)

(*) Notice: Subject to any disclaimer, the term of this patent is extended or adjusted under 35 U.S.C. 154(b) by 360 days.

(21) Appl. No.: 14/775,257

(22) PCT Filed: Mar. 14, 2014

(86) PCT No.: PCT/US2014/027691
§ 371 (c)(1),
(2) Date: Sep. 11, 2015

(87) PCT Pub. No.: WO2014/152749
PCT Pub. Date: Sep. 25, 2014

(65) Prior Publication Data
US 2016/0030297 A1    Feb. 4, 2016

Related U.S. Application Data

(60) Provisional application No. 61/784,118, filed on Mar. 14, 2013.

(51) Int. Cl.
*A61C 8/00* (2006.01)
*A61C 13/00* (2006.01)
(Continued)

(52) U.S. Cl.
CPC .............. *A61K 6/033* (2013.01); *A61C 8/005* (2013.01); *A61C 8/0006* (2013.01);
(Continued)

(58) Field of Classification Search
CPC ...... A61K 6/033; A61C 8/0006; A61C 8/005; A61C 8/0054; A61C 8/0066;
(Continued)

(56) References Cited

U.S. PATENT DOCUMENTS 2,711,021 A * 6/1955 Parker .................. A61C 8/0004
433/174
4,802,853 A * 2/1989 Krasner .................. A61C 5/00
206/83
(Continued)

FOREIGN PATENT DOCUMENTS

DE    10 2006 059 515 A1    8/2007
EP         2 095 789 A1     9/2009
(Continued)

OTHER PUBLICATIONS

Gilheany, PA, Figdor, D, Tyas, MJ; Apical Dentin Permeability and Microleakage Associated with Root End Resection and Retrograde Filling; J of Endontics; Jan. 1994; 20(1).*
(Continued)

*Primary Examiner* — Cris L. Rodriguez
*Assistant Examiner* — Mirayda A Aponte
(74) *Attorney, Agent, or Firm* — Scully, Scott, Murphy & Presser, P.C.

(57) ABSTRACT

A dental treatment method is provided. In this method, a tooth of a patient is extracted and prepared to provide a root part. A root canal in the extracted tooth is prepared and treated. A post of an abutment is fitted into the root canal to attach the root part to the abutment. The abutment having the root part is attached to a dental implant. With the root part attached to the abutment, periodontal connective tissue maintains the jaw bone associated with the extracted tooth, without significant hard tissue loss.

10 Claims, 3 Drawing Sheets

(51) Int. Cl.
*A61L 27/36* (2006.01)
*A61L 27/38* (2006.01)
*G16H 20/40* (2018.01)
*A61K 6/033* (2006.01)
*A61C 8/02* (2006.01)

(52) U.S. Cl.
CPC .......... *A61C 8/0054* (2013.01); *A61C 8/0066* (2013.01); *A61C 8/0087* (2013.01); *A61C 13/0004* (2013.01); *A61L 27/3645* (2013.01); *A61L 27/3865* (2013.01); *A61C 8/0078* (2013.01); *A61L 2430/12* (2013.01); *G16H 20/40* (2018.01)

(58) Field of Classification Search
CPC ....... A61C 8/0087; A61C 8/0078; A61C 8/00; A61C 8/0056; A61C 13/0004; A61C 2008/0084; A61C 8/0009; A61C 8/003; A61C 8/0045; A61C 8/0048; A61C 8/0075; A61C 8/0077; A61C 13/1006; A61C 13/1009; A61C 13/1016; A61L 27/3645; A61L 27/3865; A61L 2430/12
USPC ... 433/201.1, 172–175, 218–221, 204, 202.1
See application file for complete search history.

(56) References Cited

U.S. PATENT DOCUMENTS

| | | | |
|---|---|---|---|
| 5,603,616 A | 2/1997 | Fernandes | |
| 5,989,029 A * | 11/1999 | Osorio | A61C 8/005 433/173 |
| 6,129,548 A | 10/2000 | Lazzara et al. | |
| 8,246,870 B2 * | 8/2012 | Layton | A61C 8/005 264/16 |
| 2009/0042167 A1 | 2/2009 | Van Der Zel | |

FOREIGN PATENT DOCUMENTS

| | | |
|---|---|---|
| EP | 2 491 885 A1 | 8/2012 |
| GB | 2 484 992 A | 5/2012 |
| KR | 10-2010-0090564 | 8/2010 |
| RU | 2217096 C1 | 11/2003 |
| RU | 2421179 C2 | 6/2011 |

OTHER PUBLICATIONS

M. Eagle in the paper entitled "Amino acid metabolism in mammalian cell cultures", in Science, vol. 130, pp. 432-437 (1959).*
American Academy of Implant Dentistry, second paragraph—https://www.aaid-implant.org/dental-implants/what-are-dental-implants/.*
The Free Dictionary—https://medical-dictionary.thefreedictionary.com/dental+abutment.*
International Search Report dated Jul. 1, 2014 from related application PCT/US2014/027691.
Extended Supplementary European Search Report dated Oct. 13, 2016 received in European Application No. 14 76 7636.5.
European Examination Report dated Feb. 12, 2019 received in European Application No. 14 767 636.5.

* cited by examiner

DENTAL TREATMENT METHOD AND ABUTMENT USED THEREIN

CROSS-REFERENCE TO RELATED APPLICATIONS

This application is a '371 national phase of PCT/US2014/027691 filed on Mar. 14, 2014, which claims benefit of U.S. Provisional Application No. 61/784,118 filed on Mar. 14, 2013, the entire contents of which are incorporated herein by reference.

BACKGROUND

The present disclosure relates generally to dental implants, and, more particularly, to an abutment and a dental treatment methodology, which enables a professional to use autologous, preexisting tissue from tooth extraction for immediate or delayed implant placed accompanied by a prosthetic restoration.

Dental implants are becoming a preferred procedure among patients who want more durable, permanently looking teeth. From 1983 to 2008, dental implant procedures performed in the United States increased 10-fold, increasing to $150 million dental implants placed in 2008 compared to $10 million in 1988. To date, about 3 million Americans have availed themselves of dental implants and that number is growing by 500,000 per year, according to data from the American Academy of Implant Dentistry.

The basic function and osseointegration of the modern implants is achieved in most cases today. It is the more complex esthetic cases especially in the anterior with a limited bone volume where dental implants show their limitations. If a tooth is extracted in the anterior maxilla, the surrounding thin bone will be resorbed due to the surgical trauma and the lack of natural force induction. Even an immediately placed implant does not prevent this bone loss. Accordingly, many of these implants result in a soft tissue recession caused by the bone loss. This can be esthetically challenging and easily end up in mediocre results. Today, a separate bone augmentation procedure is necessary in many of these cases, in order to achieve a satisfying outcome. According to the increased demand of implants in the esthetic area, there is a need for improved implant techniques and procedures demanded by patients and dentists.

SUMMARY

According to an exemplary aspect of the present disclosure, a dental treatment method is provided. The method includes extracting a tooth of a patient; preparing the extracted tooth to provide a root part having autologous tissue; attaching the root part to an abutment, and connecting the abutment to a dental implant. For example, the abutment can be a standard premanufactured abutment or a customized abutment.

According to another exemplary aspect of the present disclosure, a method of manufacturing an abutment for a dental implant is provided. The method includes obtaining data associated with the dentition of a patient; generating a model of the abutment through a computer-implemented process based on the data; and processing a material based on the model to generate the abutment, wherein the abutment is configured to match the analogue of a predetermined tooth of the patient, such that, after the predetermined tooth is extracted and prepared to provide a root part, the root part is attached to the abutment during osseointegration.

According to still another exemplary aspect of the present disclosure, an abutment for a dental implant is provided. The abutment includes an apical end and a coronal end opposite the apical end; an insertion portion at the apical end, the insertion portion being configured to be received in an opening of the dental implant; a transition portion coronal of the insertion portion; and a connecting portion extending coronally from the transition portion. The connecting portion is configurable to be attached to a root canal or a tooth structure, which is resected from an extracted tooth of a patient.

These and other aspects and advantages of the current disclosure will become apparent from the following detailed description considered in conjunction with the accompanying drawings. It is to be understood, however, that the drawings are designed solely for purposes of illustration and not as a definition of the limits of the disclosure, for which reference should be made to the appended claims. Moreover, the drawings are not necessarily drawn to scale and, unless otherwise indicated, they are merely intended to conceptually illustrate the structures and procedures described herein.

DETAILED DESCRIPTION OF EXEMPLARY EMBODIMENTS

Detailed embodiments of the present disclosure are described herein; however, it is to be understood that the disclosed embodiments are merely illustrative of the compositions, structures and methods of the disclosure that may be embodied in various forms. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the compositions, structures and methods disclosed herein. References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment.

In this disclosure, replantation means the surgical reattachment of a body part by microsurgical means, most commonly a tooth that has been completely avulsed from a person's body. An autologous procedure means transplantation of organs, tissues or even proteins from one part of the body to another in the same individual. Tissue transplanted by the autologous procedure is referred to as an autograft or autotransplant. Auto-alloplastic implant means intentional reimplantation of an autologous tissue like a tooth with extraoral insertion of an implant (auto-alloplastic reimplantation).

Figure 1:
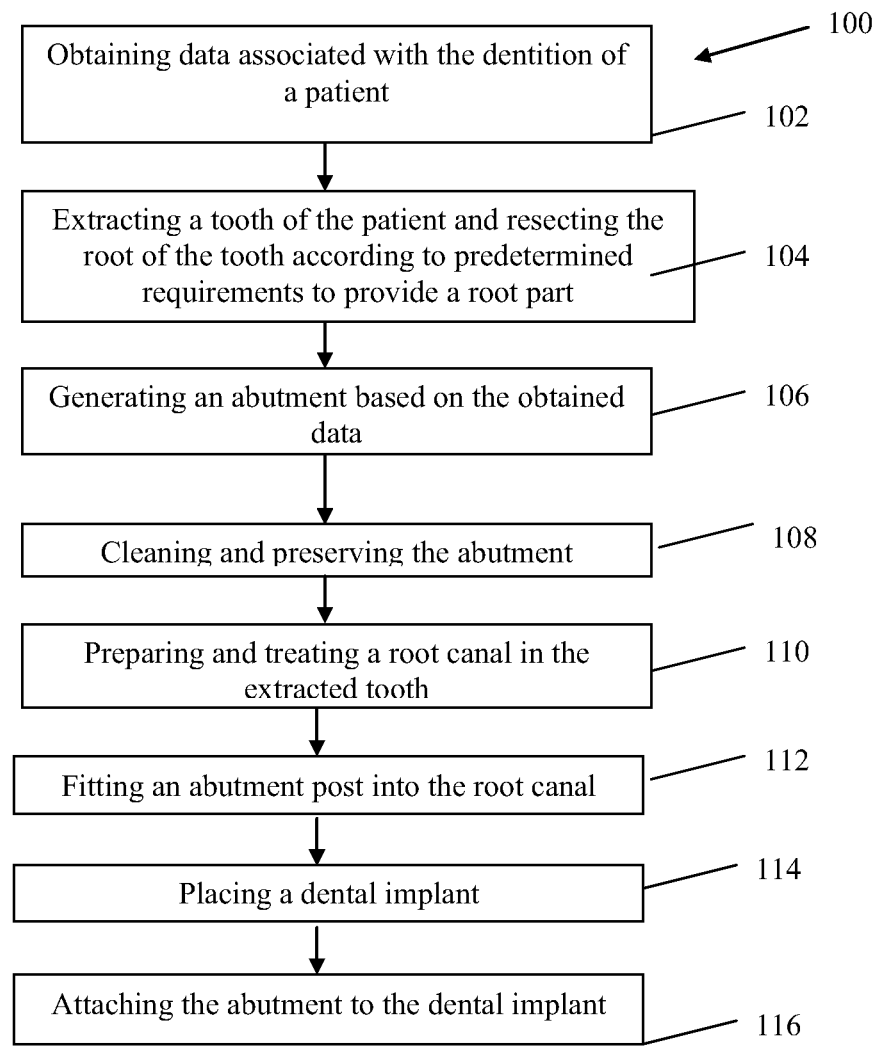
FIG. 1 is a flow chart illustrating a dental treatment method according to an exemplary aspect of the disclosure.

FIG. 1 is a flow chart illustrating steps of a dental treatment method 100 according to an exemplary aspect of the disclosure.

Figure 2:
FIG. 2 is an illustration of an X-ray scan, showing an image example of a patient's dentition captured through the scan.

At step 102, an X-ray scan is conducted to obtain data associated with the dentition of a patient, who can be adult females or males suitable for treatment with implant supported restoration at least partially in the maxilla, preferable at the age between 21 and 70. For example, the X-ray scan can be a 3D X-ray scan, such as Cone Beam Computer CT (CBCT) or classic CT. During this procedure, the field of view of the scan is limited to the treatment area in order to reduce the radiation amount exposed to the patient. FIG. 2, which is an illustration of a CBCT scan, shows an example of the patient's dentition.

If a tooth, which is compromised and will be replaced with a dental implant, is already out of the mouth, an optical scan of the tooth can be done to generate a 3D data set. The data can be used later for generating a customized abutment.

Figure 3:
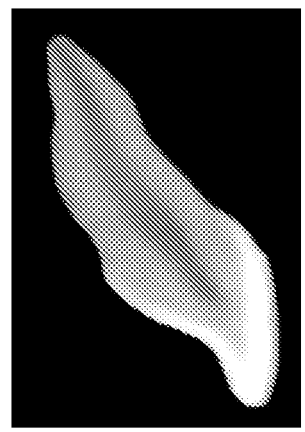
FIG. 3 is an illustration of an X-ray scan, showing an image example of an extracted tooth having a root part which will be separated from the extracted tooth.

At step 104, a tooth of the patient is extracted and prepared to provide a root part. For example, the root of the extracted tooth is resected according to predetermined requirements to provide the root part having autologous tissue attached thereon. FIG. 3 is a virtual segmentation showing an example of the extracted tooth having a root part that will be separated from the extracted tooth. During this procedure, to prevent potential fractures of the thin cortical bone layer in the anterior or premolar region at the time of extraction, a vertical extraction force is applied with very limited extra axial movements. The tooth extraction is performed as atraumatic as possible to avoid damage to the alveole.

After extraction, the tooth is intensively rinsed with a flow of sterile isotonic saline and can later be stored in a tissue culture medium at room temperature. An example of tissue culture medium is the tooth rescue box Dentosafe™ (Dentosafe GmbH, Iserlohn, Germany) can used, which is readily available. This medium maintains the vitality and proliferative capacity of periodontal ligament (PDL) cells for at least 48 hour in vitro and in vivo. During the storage period, an extra-oral endodontic treatment can be performed. To separate a part of the root of the extracted tooth, the root can be resected according to specific needs and planning of the dental implant procedure. For example, a root surface of minimum 2-3 mm is maintained. In this process, the autologous tissue, particularly the periodontal connective tissue such as PDL cells, is clinically preserved to maintain its vitality. The periodontal connective tissue, which will be eventually attached to the coronal parts of the abutment, provides most of the advantages that a periodontal connective tissue attachment confers on the natural dentition. Thus, as the periodontal connective tissue is connected to an abutment made of titanium, zirconium or PEEK, the tissue is capable of maintaining the cortical crestal bone without any significant hard tissue loss. As a result, the soft tissue level can be supported and a normal periodontal healing can be expected similar to the healing process after intentional replantation.

Figure 4:
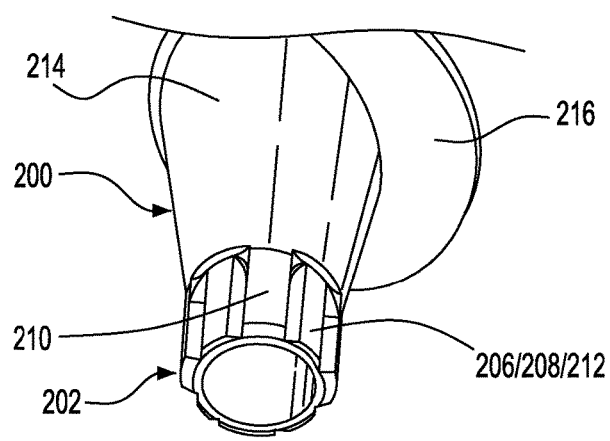
FIG. 4 is a bottom perspective view, showing an abutment according to another exemplary aspect of the disclosure, which has a customized shoulder portion fitting precisely to the shape of the extracted tooth root.

At step 106, the data resulting from the X-ray scan are imported into a computer, a processor or the like, which is capable of maintaining database and implementing a predetermined algorithm, such as CAD/CAM software. In this step, the data is processed by the computer to generate a customized abutment, to which the separated root part will be attached. During this procedure, a model of the customized abutment is first generated by the computer and, subsequently, either ceramic, acrylic like PEEK or PMMA, titanium or a metal-free zirconium material is machined based on the model to complete the customized abutment. The customized abutment is configured to match the extracted tooth in form, and accordingly, does not alter the underlying anatomy of the extraction socket, nor require any additional surgical intervention. For example, the surface of the abutment can be configured to be comparable to customized and market-available implant abutments (such as, Atlantis™ from Dentsply Implants of Tulsa, U.S.; or Procera™ from Nobel Biocare of Gothenburg, Sweden). FIG. 4 is a bottom perspective view, showing a simulated abutment having a customized base plate fitting precisely to the shape of the extracted tooth root. The customized abutments are also called Custom or Computer Milled Abutments (CMAs). CMAs can be produced before or after the implant has been placed. The CAD/CAM system allows both the dentist and the laboratory to request a site specific abutment for the patient in collaboration with a design/manufacture team. Preferably, state-of-the-art software and milling machines utilize scan data from the patient to fabricate a computer-generated abutment milled to precisely match the depth, angle and orientation of the implant and the connected natural tooth. The CMAs are available for almost all implant platforms with extreme precision. These abutments are fully milled from a block of titanium, goldplated titanium, zirconium, PEEK or acrylic material, making them extremely strong, compatible with a specific implant, and without the inaccuracies inherent in a lost wax method. Site specific instructions detailing key design features such as margin levels and emergence contours can be provided by the dentist, along with an opposing cast and bite record.

As the average diameter and shape of human teeth are well known, a standard prefabricated abutment can be used as an alternative. For every tooth in the jaw, a specific standard abutment would be available, matching this tooth specific root/crown contour and form and finally delivering a customized abutment connected to the extracted natural tooth segment.

Standard prefabricated abutments (such as, titanium abutments) are supplied by dental implant manufacturers to match their implants. The standard prefabricated abutments are also known as preparable or direct, as they are available in a variety of shapes and sizes. Angulations of the abutments may be adjusted or modified manually, either at the laboratory or in the clinical office, to adapt the shape according to the position of the implant and the patient's individual anatomy. The standard prefabricated abutment can be used (after minor adjustment if necessary) for the novel autoalloplastic abutment as disclosed by the present disclosure, which is connected to the coronal part of a natural tooth, given that the average form of every human tooth is taken into consideration and a number of different stock abutments are made available for the clinician. During a clinical treatment, the dentist selects a suitable standard prefabricated abutment, which fits best to the existing clinical situation.

Alternatively, Custom Cast Abutments (CCA) or UCLA abutments can also be used for the novel autoalloplastic abutment as disclosed by the present disclosure. An accurate impression identifies the implant position in all three planes of space. The impression is transferred directly to the laboratory where the technician fabricates a stone or plaster model and places in it an implant analog. This model and analog precisely replicates the clinical orientation and position of the implant as obtained directly from the patient's mouth. A prefabricated plastic waxing sleeve is placed in the analog and is subsequently sculpted by the technician in wax to establish proper internal fit and adaptation to the implant platform. The technician subsequently refines the wax pattern to permit the development of optimal contours and emergence profile of the abutment as well as the future implant restoration. This method permits the technician to correct for imperfect implant positions and angulations, as well as controlling the alignment of multiple implant abutments. The CCA and UCLA abutments are restorative alternatives that would enable clinicians to deliver a customized abutment connected to the natural tooth.

Alternatively, Customized Abutment with Prefabricated Elements (CAPE) can also be used for the novel autoalloplastic abutment as disclosed by the present disclosure. For example, an important aspect of an implant abutment is the mating surface that forms part of the implant-abutment connection. The design of the fitting surface and mode of abutment manufacturing will influence the precision of fit between the implant and abutment. Several issues have been identified with abutment misfit and microgaps for fully customized abutments. To justify the use, CAD/CAM customized abutments should be able to produce a degree of fit comparable with proprietary produced standard abutments. One reason for this problem is that milling machines are utilized for the manufacturing of fully customized abutments. For standard abutments mostly turning machines are used which result in a much higher accuracy compared to milling machines. The disadvantage of turning machines is the lack of free form customization, which is necessary for fully customized abutments. Therefore, the idea is to integrate both machining technologies for the production of an implant abutment, that is prefabricated in the important area of the implant-abutment connection and can be customized in the coronal area, where the ability to mimic the existing clinical situation is more important than absolute accuracy. The implant-abutment connection for every implant system is now prefabricated with a turning machine resulting in a highly precise surface comparable to the standard abutments and only the coronal part of the abutment will be customized with a milling machine, a laser sintering process or a 3D printer according to the clinical needs.

At step 108, the generated abutment is cleaned, for example, in an ultrasonic bath containing 96% ethanol for 10 min, packaged and sterilized in a steam sterilizer.

At step 110, a root canal treatment is performed from the apical direction of the extracted tooth after a standardized preparation of the root canal, and the root canal treatment is implemented through special drills offering 4 different diameters (such as, Retropost™ of Brasseler-Komet, Lemgo, Germany). At the same time, the root surface is not manipulated or processed, in order to achieve a periodontal connective tissue attachment formation.

In this procedure, the drills (or burs) and the root are intensively cooled with physiologic saline. The root canal is prepared from the apex beyond the most coronal aspect of the cemento-enamel junction. Due to the conical shape of the root canal, a generally wide preparation is required to secure a complete root canal preparation, including the marginal region of the root.

At step 112, a connecting structure of the abutment (for example, an abutment post 218 shown in FIG. 5, which will be described later) is attached to the tooth structure which is resected from the extracted tooth of a patient. For example, this step can be implemented by fitting the abutment post into the root canal. The length and dimension of the abutment post can be determined based on needs. For example, for a permanent incisor, the abutment post can be configured to allow at least 2-3 mm of the natural root surface. The intra-canal part of the abutment post is roughened to enhance cementation. After drying of the root canal through sterilized paper points, the post is cemented into the root canal with endodontic sealers to attach the extracted tooth/root part having autologous tissue (such as, PDL cells) to the abutment. Alternatively, the tooth having autologous tissue can be screwed on the abutment. During an initial setting for about 2-3 min in the air, the periodontal ligament is kept moist using sterilized paper points soaked in tissue culture medium. For primary canines, they are again stored in the tissue culture medium for at least 10 min for further setting of the sealer. Thereafter, excess sealer is removed using small excavators and sterilized dental floss. The prefabricated or customized abutment and the autologous tissue provide an embodiment of an autoalloplastic abutment.

At step 114, a dental implant is placed. For example, the dental implant can be Ankylos™ dental implants (Dentsply Implants, Tulsa, U.S.A.), which are placed according to the manufacturer's manual. The implant bed preparation and the implant placement is done minimal invasive, and particularly, the coronal bone and soft tissue is not touched. The diameter of the implant is chosen to be slightly smaller than the coronal diameter of the extraction socket, as this prevents damage to the connective tissue in this area. The length of the implant can be chosen to be longer than the extraction socket to gain primary stability.

The Ankylos™ implant is placed, for example, 2-3 mm subcrestally, to allow the formation of a periodontal connective tissue attachment. The Ankylos™ implant is FDA approved for subcrestal placement and primary stability can be achieved as checked by palpation and percussion.

Figures 5, 6:
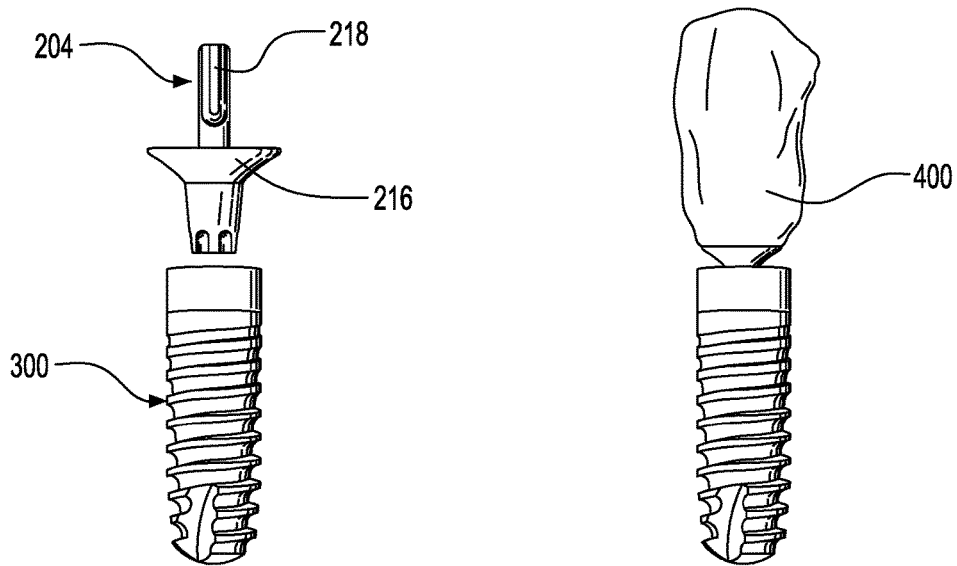
FIG. 5 is an illustration showing an implant and the abutment, prior to the connection of the abutment to the implant.
FIG. 6 is an illustration showing the implant and the abutment (with the separated tooth root attached to the abutment), after the connection of the abutment to the implant.

At step 116, the abutment is tightly connected to the implant. In this step, the remaining tooth root is cemented on the prepared customized abutment or prefabricated standard abutment. FIG. 5 illustrates the implant and the customized abutment, prior to the connection of the abutment to the implant. FIG. 6 illustrates the implant and the customized abutment (with the root part attached thereto), after the connection of the abutment to the implant. After the placement of the implant and the connection of the autoalloplastic abutment to the implant, it is desirable that the cemento-enamel junction of the tooth root cemented on the customized abutment is ideally placed slightly below the osseous margin of the alveolus, which can achieve the aim of positioning the transplant without strong contact to the bone of the alveolus. Prior to the final insertion of the combined transplant, the transplant and the transplant bed are intensively rinsed with sterile isotonic saline. Also, a customized splint (not shown in the figures), designed in accordance with the patient's lingual or vestibular anatomy, can be attached to the transplant, if there is a need to do so. The splint can provide primary stability and placement accuracy during bone integration, and loading of the implant directly after insertion is avoided. The splint is normally removed after 2-6 weeks.

Now referring back to FIGS. 4-6, an abutment 200 according to another aspect of the disclosure will be described. The abutment 200 includes an apical end 202 and a coronal end 204 opposite the apical end in the extending direction of the elongated abutment. At the apical end 202, the abutment 200 includes an insertion portion 206, which is designed to be received in an opening of a dental implant 300. The insertion portion 206 can have an anti-rotation profile 208, which for example includes a plurality of recesses 210 and projections 212 arranged alternately. The abutment 200 further includes a transition portion 214 arranged coronally of the anti-rotation profile 208. The transition portion 214 is, for example, is conically shaped to provide a better apposition between the abutment 200 and the dental implant 300. The abutment 200 further includes a shoulder portion 216 arranged coronally of the transition portion 214, and a connecting portion 218 extending coronally from the shoulder portion 216. The connecting portion can be in the form of a post. The shoulder portion 216 is customarily configurable to match the analogue of the extracted autologous tooth. A root part prepared from the extracted tooth, as identified by numeral 400, can be connected to the shoulder portion 216 or the post 218 to provide a final abutment. The abutment 200 is, for example, generated by step 106 of the method 100 as discussed above. Specifically, the shoulder portion 216 and/or the post 218 are/is configured to match the analogue of the autologous tooth, such that when the separated tooth root part 400 is cemented to the abutment 200 during the procedure, there is no need to alter the underlying anatomy of the extracted socket and there is no requirement of any additional surgical intervention. The customized abutment 200 can be manufactured through machining a stock abutment which has prefabricated features for dental implant/abutment connection and abutment/tooth part connection, respectively. For example, a stock abutment can be selected to have a prefabricated connecting portion (such as the post 218) which is used to connect to a tooth part and another prefabricated connecting portion (such as the insertion portion 206 and/or the transition portion 214) which is used to connect to a dental implant. In order to provide the customized abutment, the middle portion of the selected stock abutment is processed through subtractive and/or additive machining to provide a customized emergence profile (such as the shoulder 216), which is capable of matching the dental analogue of a specific patient.

The periodontal cells of the root can be kept vital for up to 48 hours due to the use of a special cell culture solution. In case of trauma, it will be possible to extract the compromised tooth and to keep the cells alive as long as necessary to produce the root shaped implant abutment.

The natural root provides a source of periodontal regeneration-competent cells in the postsurgical wound-healing environment, which is able to reconnect to the bone and soft tissue. The combination of a dental implant with a customized abutment fitting exactly to the autologous root tissue can reduce the overall treatment time dramatically by vertically stabilizing all surrounding tissues at the same time.

The clinical significance of the methodology is that the formation of a periodontal connective tissue attachment on the coronal parts of the dental implant abutment would provide most of the advantages that a periodontal connective tissue attachment confers on the natural dentition. The periodontal connective tissue attachment on the natural root surface connected to titanium, zirconium or PEEK abutments after immediate implant placement can potentially maintain the cortical crestal bone without any significant hard tissue loss. Consequently, the soft tissue level can be supported and the attachment type can be similar to a natural tooth; and a normal periodontal healing can be expected similar to the healing process after intentional replantation.

The clinical effect of the methodology is that the apical portion of the implant would osseo-integrate with the surrounding bone and the coronal portion with the remaining root attached to the implant abutment would form a natural connective tissue attachment. This can change the coronal tissue stability especially between two implants. Even after removal of the remaining root from the abutment or exchange of the complete abutment after the healing period, the extraction socket with the immediate implant placement has already been healed and the remaining wound surface has been minimized resulting in stabilized surrounding tissue.

While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. It is the intention, therefore, to be limited only as indicated by the scope of the claims appended hereto.

What is claimed is:

1. A dental treatment method comprising:
   extracting a tooth of a patient;
   preparing the extracted tooth to provide a root part having periodontal connective tissues attached thereon;
   attaching the root part to an abutment; and
   connecting the abutment to a dental implant.

2. The dental treatment method of claim 1, further comprising cleaning and sterilizing the abutment prior to the attaching the root part to the abutment.

3. The dental treatment method of claim 1, further comprising rinsing the extracted tooth and subsequently storing the rinsed tooth in a tissue culture medium at room temperature for at least 30 minutes to preserve the vitality of the periodontal connective tissues.

4. The dental treatment method of claim 1, wherein the periodontal connective tissues comprise periodontal ligament cells.

5. The dental treatment method of claim 1, wherein the attaching the root part to the abutment comprises preparing and treating a root canal of the extracted tooth and inserting a post of the abutment into the root canal.

6. The dental treatment method of claim 5, wherein the attaching the root part to the abutment further comprises cementing the post within the root canal after inserting the post of the abutment into the root canal.

7. The dental treatment method of claim 5, wherein the attaching the root part to the abutment comprises threading the post of the abutment into the root canal.

8. The dental treatment method of claim 1, wherein the preparing the extracted tooth to provide the root part having the periodontal connective tissues comprises resecting the root of the extracted tooth to maintain a root surface of at least 2-3 mm in the direction from the apical end to the coronal end of the extracted tooth.

9. The dental treatment method of claim 1, further comprising placing the dental implant into an extraction socket of the patient prior to the connecting the abutment to the dental implant.

10. The dental treatment method of claim 9, wherein the implant is placed 2-3 mm subcrestally to allow attachment of periodontal connective tissues on the dental implant.

\* \* \* \* \*